United States Patent [19]
Reznik et al.

[11] 3,937,829
[45] Feb. 10, 1976

[54] MEDICINAL PREPARATION FOR TREATMENT OF VARIOUS FORMS OF LEPROSY

[76] Inventors: Vladimir Savich Reznik, ulitsa Gospitalnaya 34, kv. 34; Nikolai Grigorievich Pashkurov, ulitsa Druzhby 6, kv. 20; Abdurakhim Abdurakhimovich Muslinkin, ulitsa Zhdanova 60, kv. 33, all of Kazan; Elena Nikolaevna Zhurkina, prospekt Kosmonavtov 86, kv. 48, Leningrad; Nikolai Mikhailovich Goloschapov, ulitsa Druzhby, 9, kv. 110, Zagorsk; Vladimir Konstantinovich Steklovsky, Zagorsky raion, p/o Krasnozavodsk, Moskovskaya oblast, all of U.S.S.R.

[22] Filed: Aug. 31, 1973

[21] Appl. No.: 393,676

[52] U.S. Cl. .............................................. 424/250
[51] Int. Cl.² ...................................... A61K 31/495
[58] Field of Search ..................................... 424/250

[56] References Cited
OTHER PUBLICATIONS
*Chemical Abstracts,* 76:59464b (1972).

*Primary Examiner*—Jerome D. Goldberg
*Attorney, Agent, or Firm*—Haseltine, Lake & Waters

[57] ABSTRACT

A medicinal preparation for treatment of various forms of leprosy, containing as the active principle, p,p bis-(2,4-dioxy-6-methylpyrimidinyl-5-sulfonamido)diphenylsulfone of the following formula:

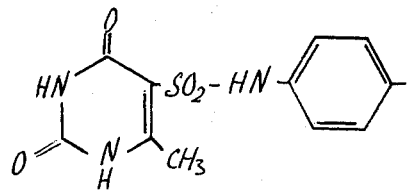

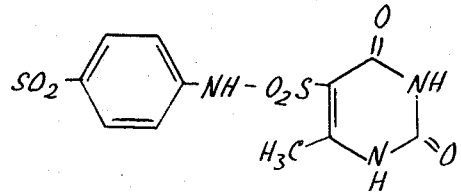

12 Claims, No Drawings

MEDICINAL PREPARATION FOR TREATMENT OF VARIOUS FORMS OF LEPROSY

The present invention is concerned with a novel medicinal preparation for treatment of various forms of leprosy.

Known in medical practice are the following preparations for said purposes: sulphonic preparations (diamino-diphenylsulfone, sulphetrone, diacetyl-diamonodiphenylsulfone); sulphonylamides (sulphadimethoxin, sulphalene, sulphomethoxin); phenazine derivatives (clophazimine or lymprene). The most effective preparations among all those stated above are the sulfonic ones.

Said preparations, sulfonic inclusive, are toxic and possess side effects upon hemopoietic organs (anemia), the function of the liver (sometimes down to an acute parenchymatous hepatitis), as well as depress the protective power of the organism.

Administration of the aforesaid preparations concurrently with vitamins, biopreparations, stimulants, preparations of Fe, As, etc. reduces but slightly their toxic action.

It is therefore an essential object of the present invention to provide a novel medicinal preparation for treatment of various forms of leprosy, possessing a reasonably wide range of therapeutic effect.

It is another object of the present invention to provide a medicinal preparation for treatment of various forms of leprosy, stimulating hemopoiesis, the function of the liver and protective ability of the human organism.

In accordance with said and other objects the invention resides in that the herein-proposed medicinal preparation contains as the active principle p,-p-bis(2,4-dioxy-6-methylpyrimidinyl-5-sulfonamido)diphenylsulfone of the following formula:

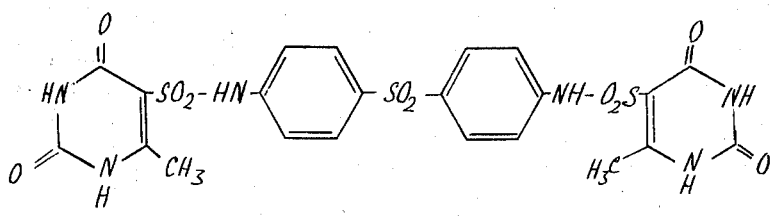

Said preparation is essentially a light-yellow finely crystalline odorless powder having a slightly bitterish taste, sparingly soluble in water, physiological saline, 0.1-1-percent aqueous novocain solution, insoluble in ethyl alcohol. The preparation is soluble in diluted alkalis, dimethylformamide and dimethysulfoxide. Aqueous solutions of the preparation give an acid reaction. M.p. of the preparation lies at 233°–234°C, at temperatures above 235°C it decomposes; the preparation withstands heating at 150°C during 2 hours, at 100°C during 5 hours without decomposition.

Toxicity of the preparation with respect to warm-blooded animals (white mice, rats, cats) features $LD_{50}$ = 2600 mg/kg body weight which is one-fifth the toxicity of the principal antileprotic medicine, viz., diaminodiphenylsulfone.

The present medicinal preparation is recommended to be administered internally both per se and in combination with inert carriers for tablets. Examples of such carriers are sugar, starch, baking soda, barium salts.

It is expedient ot use tablets containing 0.1–0.3 g of the active principle.

When administered parenterally (for intramuscular and subcutaneous injections) the preparation is recommended to comprise the aforesaid active principle in conjunction with solvents such as distilled water, physiological saline or 0.1-1.0-percent aqueous novocain. It is expedient that use be made of solutions containing 1-12 weight percent of the active principle.

Under ambulant-therapy conditions, alongside with internal administration of the preparation in the form of powder or tablets, also parenteral administration of the preparation is practicable, containing the active principle in combination with sunflower-seed, castor, vaseline, camphor, or chaulmoogra oil. Content of the active principle in emulsions is expedient to vary within 10 to 25 weight percent depending upon each particular case.

In some cases, depending upon medical indications, it is recommendable to use the preparation containing the active principle in conjunction with a pharmaceutical excipient for suppositories which is a mixture of cocoa oil with anhydrous lanolin. It is expedient that suppositories be used having the content of the active principle from 5 to 15 weight percent.

Toxico-biological action of the preparation was studied in animals of the three species, viz., white mice, rats and cats. As a result, it was established that introduction of the medicinal preparation into an animal's organism during a three-month period provokes no changes, according to the data of biochemical and histomorphological analyses, in the internal organs, endocrine glands, brain, nerves and blood as compared to the control animals.

There was studied the influence of the preparation upon the synthesis of RNA in the lymphocytes of the human peripheral blood and in the cell culture of the rat's spleen and established that the present medicinal preparation promotes the synthesis of RNA in the lymphocytes of the human peripheral blood. This may be considered as an evidence of possible differentiation of the lymphocytes or of potentiation of their specific function under the effect of the preparation. In its turn, the latter fact testifies to the fact that the preparation is non-toxic and acts as a stimulant of the protective power of the organisms by virtue of an increased immune response.

These data do not exclude the possibility of either bacteriostatic or bactericidal effect of the preparation upon the causative agent of leprose.

Cinical experiments were conducted on 99 patients, of which 92 suffered from lepromatous leprosy, 5 patients, from the reactive tuberculoid form of the disease and 2 patients, from tuberculoid leprosy.

Treatment was applied for 54 months. According to the duration of the disease the patients fell into the following groups: under 5 years – 18 persons, from 6 to 10 years – 20, from 11 to 20 years – 40, and over 20 years – 21 patients.

The majority of patients had previously been treated with other antileprotics; some patients showed drug resistance with respect to antileprotic preparations.

The lepric process was characterized by diffuse and focal infiltration, while histological examination revealed specific granuloma with a great number of *Mycobacterium leprae*.

Patients were administered the medicinal preparation in doses of 0.1, 0.2, and 0.3 g as powder or tablets b.i.d. or t.i.d. some patients were administered the preparation intramuscularly in a dose of 2-3 ml of 1-12 percent solution of the active principle in water, physiological saline or in a 0.5 percent aqueous novocain. Clinical examinations showed the best therapeutic result to be obtained when administering a 10 percent solution of the preparation in distilled water. Any attempt to obtain solutions with the concentration of the active principle in excess of 12 wt.% results in falling out of the substance as a precipitate.

In the course of treatment, leprous reactions in the patients, as well as neurites, inflammatory processes of the mucous membranes in the nose, throat, eye, etc. disappeared.

The regress of the disease started in 3-6 weeks and was characterized by the resolution of infiltrates and lepromas, appearance of a great amount of granular forms of the causative agent and bacterial decomposition, as well as occurrence of a sharply marked fibrosis both along the periphery of the foci of lesion and at the center thereof.

In analyzing clinico-biochemical data there was noted the sharply pronounced antipyretic effect of the preparation and (though less manifested) the anabolic effect thereof.

In 7 patients during the course of treatment a transformation of the lepromatous form of the disease into the tuberculoid form occurred, which was evidenced by the disclosure of the tuberculoid structure in histological examinations conducted during the course of treatment.

In all patients resistant to sulfonic antileprotic preparations, a good therapeutic effect was observed.

None of the 36 patients dismissed for ambulant therapy, showed a recurrence of the disease during the following four years.

In addition, the preparation was applied as emulsions based on sunflower-seed, castor, vaseline, camphor or chaulmoogra oil. When the preparation was administered as emulsions, best results were observed from the introduction of emulsions containing 20 wt.% of the active principle based upon sunflower-seed, camphor or castor oil. Said emulsions were injected intramuscularly once or twice per week.

In some individual patients, according to medical indications, the preparation was applied as suppositories containing 5-15 wt.% of the active principle. No irritating effect upon the mucous membranes was observed, whereas a markedly pronounced antipyretic action was rendered.

During many-year treatment none of the patients was found to suffer from any side effect of the preparation irrespective of the form in which it was administered (i.e., powder, tablets solutions, emulsions or suppositories).

Contraindications for the application of the preparation are terminal stages of the disease, grave affections of the kidneys or cardiovascular system accompanied by renal or cardiovascular insufficiency.

The medicinal preparation according to the invention for treatment of various forms of leprosy is stable when under long-term storage. Check samples of the preparation stored in darkness at 18°-25°C during 5 years, were found to retain the appearance, melting point, IR-spectrum data, solubility and pH value of an aqueous solution.

The preparation has to be stored in dark-glass jars closed by covers. When under storage the preparation must be protected against direct sunlight and abnormal ambient-air humidity.

In addition to the specific therapeutic effect the preparation also promotes the processes of intracellular metabolism, enhances the quantity of RNA in a cell which leads to an easier differentiation of the lymphocytes into phagocytic forms and to the completion of phagocytosis that is heavily depressed in patients suffering from the lepromatous form of leprosy. This contributes to the transformation of the lepromatous form of the disease into the tuberculoid one.

In the course of treatment patients show an increased amount of erythrocytes, higher percentage of hemoglobin and normalized protein metabolism. The latter is of special importance, since leprotic patients suffer from hypoalbuminemia.

Besides, the proposed preparation proves to be effective also in treatment of patients resistant to sulfonic or some other antileprotic therapy.

When determining the concentration of sulfonic preparations in the blood during treatment with diaminodiphenylsulfone, sulphetrone and the inventive preparations, it was observed that the concentration of the inventive preparation is twelve times as high as that of diaminodiphenylsulfone, both being administered as a powder at a dose of 0.1 g s.i.d. Futhermore, Injection of 2 ml of a 10 percent solution of the inventive preparation gave a concentration in the blood four times that which resulted from the introduction of 1 ml of 15-10 percent solution of sulphetrone.

High specific activity, absence of any harmful side effects, as well as stimulating effect upon the protective power of the human organism, all this enables the inventive medicinal preparation for treatment of various forms of leprosy to be considered as the most effective of the all heretofore known antileprotics.

What is claimed is:

1. A medicinal preparation for the treatment of various forms of leprosy, containing as the active principle p,p bis-(2,4-dioxy-6-methylpyrimidinyl5-sulfonamido) diphenyl sulfone of the formula:

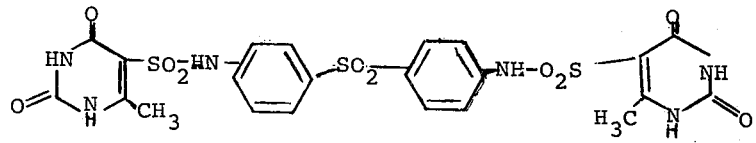

in an amount effective for treating leprosy in combination with physiological saline solution.

2. A medcinal preparation as claimed in claim 1, containing the active principle in an amount of 1-12 wt.%.

3. A medicinal preparation for the treatment of various forms of leprosy, containing as the active principle p,p bis-(2,4-dioxy-6-methylpyrimidinyl-5-sulfonamido) diphenyl sulfone of the formula:

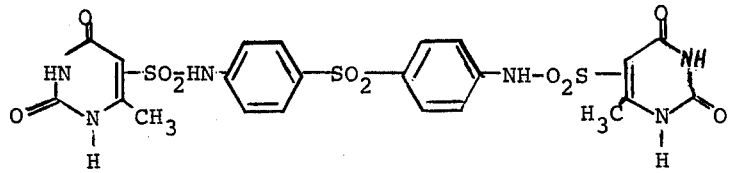

in an amount effective for treating leprosy in combination with a 0.1–1 percent novocain solution.

4. A medicinal preparation for the treatment of various forms of leprosy, containing as the active principle p,p bis-(2,4-dioxy-6-methyl-pyrimidnyl-5-sulfonamido)diphenyl sulfone of the formula:

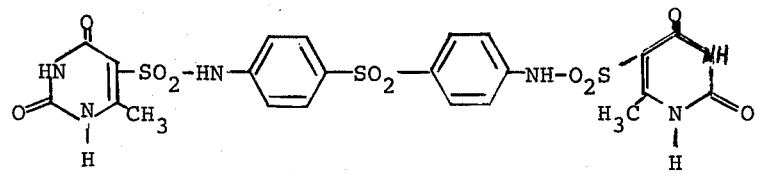

in an amount effective for treating leprosy in combination with a pharmaceutically acceptable carrier in the form of a tablet.

5. A medicinal preparation as claimed in claim 4, containing the active principle in an amount of 0.1–0.3 g.

6. A medicinal preparation for the treatment of various forms of leprosy, containing as the active principle p,p bis-(2,4-dioxy-6-methyl-pyrimidinyl-5-sulfonamido) diphenyl sulfone of the formula:

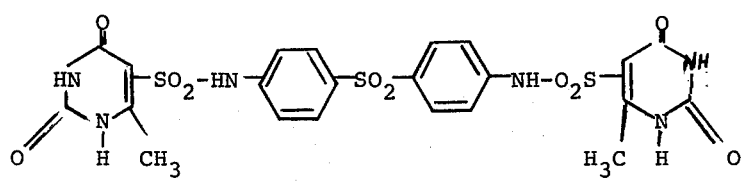

in an amount effective for treating leprosy in combination with a pharmaceutically acceptable carrier in the form of an emulsion.

7. A medicinal preparation according to claim 6 containing the active principle in an amount of 1–12%.

8. A medicinal preparation as claimed in claim 7, containing the active principle in an amount of 10–25 wt.%.

9. A medicinal preparation for the treatment of various forms of leprosy, containing as the active principle p,p bis-(2,4-dioxy-6-methyl-pyrimidindyl-5-sulfonamido) diphenyl sulfone of the formula:

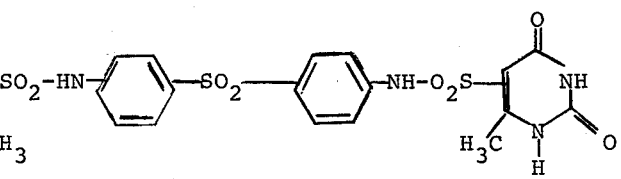

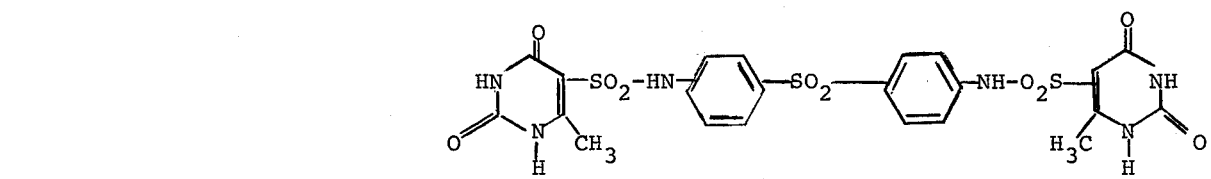

in an amount effective for treating leprosy in combination with a pharmaceutically acceptable carrier in the form of a suppository.

10. A medicinal preparation as claimed in claim 9, containing the active principle in an amount of 5–15 wt.%.

11. A method for the treatment of leprosy in humans comprising administering internally or parenterally a composition comprising an amount effective against leprosy of p,p-bis(2,4-dioxy-6-methylpyrimidinyl-5-sulfonamido) diphenyl sulfone of the formula:

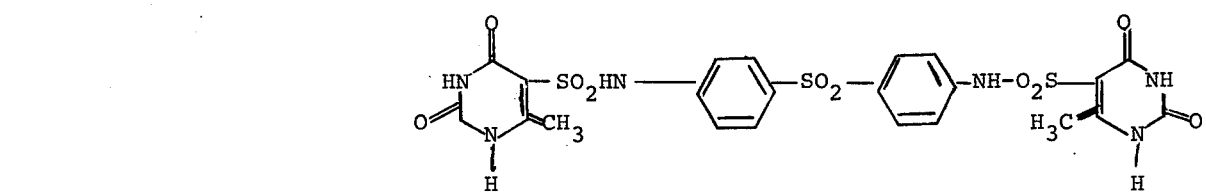

12. A method according to claim 11 wherein the composition comprises a pharamceutically acceptable solid or liquid carrier.

* * * * *